United States Patent
Tayeb et al.

(10) Patent No.: US 11,364,199 B1
(45) Date of Patent: Jun. 21, 2022

(54) ESSENTIAL OIL NANOEMULSION AND METHODS OF USE THEREOF

(71) Applicant: King Abdulaziz University, Jeddah (SA)

(72) Inventors: Hossam H. Tayeb, Jeddah (SA); Raed Felimban, Jeddah (SA); Nojod Hasaballah, Jeddah (SA); Jwana Bin Mahfouz, Jeddah (SA); Adeel Chaudhary, Jeddah (SA); Majed Felemban, Jeddah (SA); Fuad Alnadwi, Jeddah (SA); Waleed Rizg, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/522,338

(22) Filed: Nov. 9, 2021

(51) Int. Cl.
| | | |
|---|---|---|
| *A61K 9/107* | (2006.01) | |
| *A61K 36/185* | (2006.01) | |
| *A61K 47/26* | (2006.01) | |
| *A61K 47/10* | (2017.01) | |

(52) U.S. Cl.
CPC .......... *A61K 9/1075* (2013.01); *A61K 36/185* (2013.01); *A61K 47/10* (2013.01); *A61K 47/26* (2013.01)

(58) Field of Classification Search
CPC .... A61K 9/1075; A61K 36/185; A61K 47/10; A61K 47/26
See application file for complete search history.

(56) References Cited

U.S. PATENT DOCUMENTS

| | | | |
|---|---|---|---|
| 2001/0036450 A1 | 11/2001 | Verite et al. | |
| 2010/0111884 A1* | 5/2010 | Acker | A61Q 17/04 424/59 |
| 2013/0273123 A1 | 10/2013 | Blume et al. | |

FOREIGN PATENT DOCUMENTS

| | | | | |
|---|---|---|---|---|
| WO | WO-0059475 A1 * | 10/2000 | ............. | A61K 47/02 |
| WO | 2015066777 | 5/2014 | | |

OTHER PUBLICATIONS

Pham et al., "Preparation of Tamanu Oil Nanoemulsions by Phase Inversion Temperature", 2020 IOP Conf. Ser.: Mater. Sci. Eng. 991 012116.
Thakur et al., "Nanoemulsion in Enhancement of Bioavailability of Poorly Soluble Drugs: A Review", Pharmacophore 2013, vol. 4 (1), 15-25.
Urbankova et al., "Caseinate-Stabilized Emulsions of Black Cumin and Tamanu Oils: Preparation, Characterization and Antibacterial Activity", Polymers 2019, 11, 1951.

* cited by examiner

*Primary Examiner* — Robert A Wax
*Assistant Examiner* — Quanglong N Truong
(74) *Attorney, Agent, or Firm* — WCF IP

(57) ABSTRACT

An oil-in-water nanoemulsion is provided. The nanoemulsion contains 8-12% w/v essential oil, 1-5% w/v polysorbate 80 surfactant, 2-6% w/v glyceryl citrate/lactate/linoleate/oleate co-surfactant, and 1-5% w/v glycerol monocaprylate, type I, wherein a ratio of the surfactant and co-surfactant to essential oil is from 1:1.1 to 1:1.6. Methods of preparing the nanoemulsion and for the transdermal delivery of the nanoemulsion are also provided.

2 Claims, 7 Drawing Sheets

ESSENTIAL OIL NANOEMULSION AND METHODS OF USE THEREOF

FIELD OF THE INVENTION

The invention is generally related to oil-in-water nanoemulsions for the transdermal delivery of essential oils such as tamanu oil.

BACKGROUND OF THE INVENTION

Topical dermal drug delivery using soft colloidal nanomaterials, such as liposomes and nanoemulsions (NEs), offer advantages including better drug penetration and absorption, bioavailability, non-invasive administration, self-medication, and minimized side effects [1]. NEs are heterogenous systems of two unmixable liquids, containing hydrophobic and hydrophilic phases, and surfactants or stabilizers. NEs are classified based on the dispersed phase (core) as single, oil in water (O/W) or water in oil (W/O), and double, oil in water in oil (O/W/O) or water in oil in water (W/O/W), emulsions. NEs are manufactured using high (e.g., ultrasonicators and homogenizers) and low shearing (e.g., phase inversion temperature and phase inversion composition) methods [2]. The average droplet size of NEs ranges from 20-500 nm, which is considered an important parameter in enhancing the bioavailability of natural compounds through topical delivery [3]. NEs have many advantages as a topical drug delivery system including high loading capacity of hydrophobic and hydrophilic compounds, enhanced skin permeation, penetration, and protection of encapsulated cargos, lower side effects, high surface area that allows for better bio-interaction with targeted tissues. These advantages, and the long-term safety profile of NEs in various fields including cosmetics, food industry and medicine demonstrate their potential as carriers of bioactive compounds, particularly toward dermatological applications.

Essential oils (EOs) are complex plant extracts comprising various components and chemicals. A breakdown of an EO using analytical systems, such as gas chromatography, can reveal many substances. It has been reported that almost 4000 chemical compounds were found in EOs. The composition of extracted EOs varies based on extraction methods and the origin of plant samples. Terpenes and their subclasses, like phenols, alcohols, and aldehydes, are the most common compounds found in EOs. EOs and their bioactive compounds have been historically applied as herbal medicine against many health problems including dermal diseases due to their innate anticancer, antibacterial, antifungal, antiviral, anti-inflammatory, and antioxidant effects [4]. However, EOs have many drawbacks including toxicity, instability, volatility, light sensitivity, and low aqueous solubility. The encapsulation of EO within nanocarriers can enhance their physical and chemical properties, offering protection against surrounding environment effects including light and air exposure, spoilage, and volatilization. Nanocarriers can also improve the therapeutic efficacy of EOs through enhancing bioavailability, release profiles, biological stability, solubility, and localization at the target site within the human body [5].

Calophyllum inophyllum L. (Calophyllaceae) oil, also called tamanu oil (TMO), is extracted from a pantropical tree commonly found in Africa, Asia, and Pacific countries [6]. The composition of TMO comprises various bioactive compounds including fatty acids, like stearate, palmitate, oleate, and lineolate. Therefore, TMO has been utilized traditionally in various applications including dermatology against skin and mucous membrane disorders. It has been reported that TMO has therapeutic potential against dermatological diseases such as burns, dermatoses, eczema, acne, psoriasis, and microbial skin infections [7, 8]. This because TMO possesses innate antibiotic properties due to the presence of calophyllic acid and lactone. TMO has also been applied traditionally, topically for rheumatism and sciatica relief during massages because of its soothing, calming, and pain-relieving capabilities owing to the presence of secondary bioactive compounds including triterpenes, flavonoids and xanthones. Antimicrobial naturotherapy applications are also possible for the treatment of wounds [8], and as regenerative or analgesics due to the presence of coumarin derivatives in TMO. TMO has been proven to have an antioxidant activity by lowering intracellular reactive oxygen species. The absorptive capacity of TMO for UV radiation made it an important element in the manufacturing of dermal formulation [9]. In addition, TMO has been shown to have antimicrobial properties, including antibacterial and antifungal actions, particularly against pathogenic skin strains such as *S. aureus* and *S. pyogenes* [10]. Calophyllolide, a compound derived from TMO, was found to reduce myeloperoxidase activity, and downregulate pro-inflammatory cytokines and increase anti-inflammatory cytokines [7, 11]. It was also reported that TMO can prevent fibrosis formation in a mouse model and efficiently promote the wound healing process.

In contrast, the advantages of TMO are limited by the presence of fatty acids, which are prone to chemical changes resulting from external factors such as light exposure or oxidation. TMO hydrophobicity also affects its pharmaceutical application through various routes of administration, like the intravenous route.

Two studies have explored the use of TMO to formulate a nanoemulsion. Urbánková, Lucie et al. have used a protein-based surfactant, caseinate, to formulate emulsions of TMO using both homogenization and sonication. The resulting droplet size for the TMO emulsion ranges from 0.4 to 1.5 µm respectively based on the composition and the emulsification method. Disc diffusion was applied to investigated antimicrobial activity of the tamanu oil emulsion. 30% of TMO emulsions with two different caseinate concentrations were used for this experiment for both emulsions of gram-positive bacteria. Zone of inhibition were observed [12]. Another study described a phase inversion temperature method to produce TMO nanoemulsion. The stabilisers or surfactants investigated to produce emulsions are Tween 20, Tween 40, or Tween 80. The study found that Tween 80 can make stable emulsions. The study reported that at least 1.5:1 or more surfactant-to-oil ratio is needed to produce an emulsion with particle sizes lower than 100 nm. The stability study shows that the developed nanoemulsion was not stable at room temperature after one month of incubation. Also, at least a 3:1 surfactant-to-oil ratio is needed to maintain one month stability of the developed emulsion at 4° C. [13].

Therefore, improved nanoemulsions for the delivery of essential oils are needed.

SUMMARY

Described herein is oil-in-water nanoemulsions having long-term stability against surrounding physical and biological environments. The nanoemulsions may be applied as liquid or gel forms for the treatment of various skin diseases including microbial infections, wound healing, and UV protection. The nanoemulsions are a safe antimicrobial drug delivery system of essential oils and other hydrophobic compounds.

An aspect of the disclosure provides an oil-in-water nanoemulsion, comprising 8-12% w/v essential oil, 1-5% w/v polysorbate 80 surfactant, 2-6% w/v glyceryl citrate/lactate/linoleate/oleate co-surfactant, and 1-5% w/v glycerol monocaprylate, type I, wherein a ratio of the surfactant and co-surfactant to essential oil is from 1:1.1 to 1:1.6. In some embodiments, the essential oil comprises tamanu oil. In some embodiments, the nanoemulsion comprises 10% w/v essential oil, 3% w/v polysorbate 80 surfactant, 4% w/v glyceryl citrate/lactate/linoleate/oleate co-surfactant, and 2% w/v glycerol monocaprylate, type I, wherein the ratio of the surfactant and co-surfactant to essential oil is 1:1.4.

In some embodiments, the nanoemulsion has an average droplet size of 90-105 nm. In some embodiments, the nanoemulsion has a surface charge of −55 to −65 mV. In some embodiments, the nanoemulsion remains stable at a temperature from 4-37° C. for at least 30 days such that an average droplet size of the nanoemulsion does not increase more than 10 nm. In some embodiments, the nanoemulsion remains stable at a pH from 4-7 for at least 30 days such that an average droplet size of the nanoemulsion does not increase more than 10 nm.

Another aspect of the disclosure provides a dosage form comprising a nanoemulsion as described herein, wherein the dosage form can be formulated as a gel or cream.

Another aspect of the disclosure provides a method for the transdermal delivery of an essential oil to a subject in need thereof, comprising topically administering an oil-in-water nanoemulsion as described herein to the subject. In some embodiments, the essential oil comprises tamanu oil and the nanoemulsion is administered to treat a skin infection. In some embodiments, the essential oil comprises tamanu oil and the emulsion is administered to treat a wound.

Another aspect of the disclosure provides a method of preparing an oil-in-water nanoemulsion as described herein, comprising adding a dispersed phase to a continuous phase to provide a combined sample, wherein the dispersed phase comprises the essential oil, the co-surfactant, and glycerol monocaprylate, type I and wherein the continuous phase comprises the surfactant and water; and sonicating the combined sample under conditions sufficient to produce the oil-in-water nanoemulsion.

DETAILED DESCRIPTION

Figure 1:
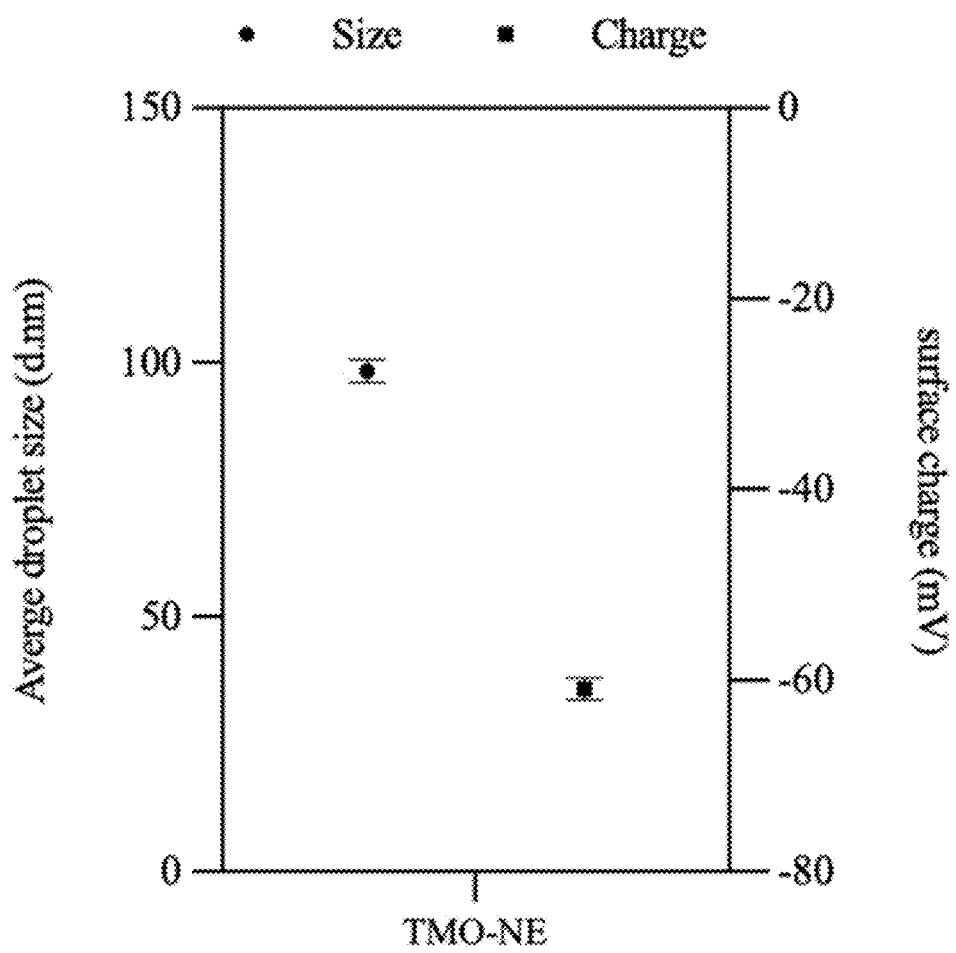
FIG. 1. Physio-chemical characterization of the tamanu oil-based nanoemulsion (TMO-NE).

Embodiments of the disclosure provide a nanoemulsion as a topical, skin drug delivery system comprising an essential oil, surfactant, cosurfactant and penetration enhancer of water-insoluble active pharmaceutical ingredients. The nanoemulsion improves the physiochemical and pharmaceutical properties including absorption and stability of hydrophobic compounds, particularly tamanu oil (TMO) and other essential oils that have therapeutic properties for skin including stimulation of collagen formation, UV-light protection, wound healing, antimicrobial and antioxidation effects. In particular, the composition of this stable nanoemulsion formulation allows for the encapsulation of various essential oils having different viscosities and concentrations. The essential oil is dispersed in the aqueous phase (water) and stabilized using a surfactant and co-surfactant. A skin penetration enhancer provides better absorption of essential oil bioactive compounds, thus enhancing drug delivery for dermatological disorders. As shown in the Example, the nanoemulsions described herein have an enhanced proliferation effect on human neonatal dermal fibroblasts (HNDFs) at low concentrations of the loaded essential. A potent antimicrobial effect on one of the most common causative agents of skin infections, *S. aureus*, was also demonstrated. The nanoemulstion may be prepared from generally recognized as safe materials (GRAS) or safe for human use compounds toward dermatology, particularly antimicrobial applications.

An emulsion contains two immiscible liquids, which are finely dispersed in each other. For oil-in water emulsions, the oily phase (dispersed phase) is evenly mixed into the aqueous phase (continuous phase).

Essential oils are concentrated hydrophobic liquids containing volatile (easily evaporated at normal temperatures) chemical compounds from plants. Essential oils are also known as volatile oils, ethereal oils, aetheroleum, or simply as the oil of the plant from which they were extracted, such as oil of clove. An essential oil is "essential" in the sense that it contains the "essence of" the plant's fragrance—the characteristic fragrance of the plant from which it is derived. Essential oils are generally extracted by distillation, often by using steam. Other processes include expression, solvent extraction, sfumatura, absolute oil extraction, resin tapping, wax embedding, and cold pressing. Exemplary essential oils or essential oil constituents that may be incorporated into the nanoemulsion include, but are not limited to, tamanu oil, henna oil, onion oil, carrier oils such as Miglyol 812, clove oil, coriander oil, cymbopogon oil, sweet orange oil, thyme oil, citronella oil, rose oil, palmarosa oil, red deadnettle oil, hedgenettle oil, cinnamon bark oil, cardamom oil, marjoram oil, orange oil, camphor laurel wood oil, pine oil, β-caryophyllene, eugenol, eugenol acetate, carvacrol, linalool, thymol, geraniol, geranyl acetate, bicyclogermacrene, cinnamaldehyde, geranial, neral, 1,8-cineole, methyl chavicol, methyl cinnamate, methyl eugenol, camphor, α-thujone, viridiflorol, limonene, (Z)-linalool oxide, α-pinene, p-cymene, (E)-caryophyllene, and γ-terpinene. In some embodiments, the composition contains 6-14% w/v essential oil, e.g. about 8-12% w/v essential oil, e.g. about 10% w/v. In some embodiments, the formulation may also include hydrophobic natural or chemical drugs.

The nanoemulsion also includes two or more surfactants, e.g. polysorbates, sorbitan esters of fatty acids, cetearyl glucoside or poloxamers or other stabilisers such as xanthan gum, or propylene glycol alginate. In some embodiments, the surfactant is selected from sorbitan monopalmitate 20, sorbitan monopalmitate 40, sorbitan monopalmitate 80, polysorbate 20, polysorbate 60, polysorbate 80, or glyceryl citrate/lactate/linoleate/oleate (Imwitor® 375 which may be sunflower-based). In some embodiments, the total amount of surfactants in the compositions of the presently disclosed embodiments is about 4-10% w/v of the total composition, e.g. 6-8% w/v. In some embodiments, the composition contains 1-5% w/v surfactant (e.g. polysorbate 80) and 2-6% w/v co-surfactant (e.g. glyceryl citrate/lactate/linoleate/oleate).

Surfactants are substances that are amphipathic, which means that they contain both hydrophobic and hydrophilic groups. The hydrophilic-lipophilic balance (HLB) of a surfactant is measured on an empirical scale developed by Griffin (W. C. Griffin, J. Cosmet. Chem., 1, 311, 1949). This scale ranges from 0 to 20, with 0 for a completely lipophilic molecule and 20 for a completely hydrophilic molecule. In some embodiments, the surfactant has a HLB value of about 9-16, e.g. about 10-15.

In some embodiments, a ratio of the surfactant and co-surfactant to essential oil is from 1:1.1 to 1:1.6, e.g. about 1:1.4.

Permeation enhancers are molecules that interact with the constituents of the skin's outermost and rate limiting layer stratum corneum (SC), and increase its permeability. In a preferred embodiment, the formulation of the disclosure utilizes glycerol monocaprylate, type I (Imwitor® 988 which may be derived from vegetable sources) as a permeation enhancer. Alternative or additional skin penetration enhancers which may be incorporated into the nanoemulsion include, but are not limited to, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG), surfactants and terpenes (e.g. citral). In some embodiments, the permeation enhancer is present at a concentration of 1-5% w/v, e.g. 2-4% w/v, e.g. about 2% w/v.

In some embodiments, the nanoemulsion described herein has an average droplet size of 90-105 nm. In some embodiments, the nanoemulsion has a surface charge of −55 to −65 mV or higher. The negative surface charge provides for increased electrostatic stability of the nanoemulsion at various temperatures and pH conditions, e.g. at skin pH ranges. In some embodiments, the nanoemulsion remains stable at a temperature from 4-37° C. for at least 7 days, e.g. at least 30-100 days, such that an average droplet size of the nanoemulsion does not increase more than 1-10 nm. In some embodiments, the nanoemulsion remains stable at a pH from 3-8, e.g. from 4-7 for at least 7 days, e.g. at least 30-100 days, such that an average droplet size of the nanoemulsion does not increase more than 1-10 nm.

Another aspect of the disclosure provides a dosage form comprising a nanoemulsion as described herein, wherein the dosage form is formulated as a gel or cream. A composition comprising the nanoemulsion may contain one or more pharmaceutically acceptable carriers. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

The compositions of the present disclosure may also contain other components such as, but not limited to, antioxidants, additives, adjuvants, buffers, tonicity agents, bioadhesive polymers, and preservatives. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure include methods of preparing compositions as described herein. The method may comprise adding a dispersed phase to a continuous phase to provide a combined sample, wherein the dispersed phase comprises the essential oil, the co-surfactant, and penetration enhancer and wherein the continuous phase comprises the surfactant and water; and sonicating the combined sample under conditions sufficient to produce the oil-in-water nanoemulsion. The ultrasonication high-shearing method is applied to generate disruptive energy to disperse the essential oil into the aqueous phase and to form nano-sized droplets. Other preparation methods known in the art include emulsifying techniques such as high-pressure homogenization, high-shear mixing, and microfluidization.

The formulations described herein are useful for delivery of a substantially insoluble or sparingly soluble biologically active agent to a human or non-human animal subject. In some embodiments, the active agent has a solubility in water (w/v) which is 3% or less, e.g. 1% or less.

The present disclosure also provides a method for the transdermal delivery of an essential oil or other hydrophobic compound to a subject in need thereof, comprising topically administering an oil-in-water nanoemulsion as described herein to the subject. The compositions of the disclosure may be useful for the treatment of any disease or disorder that the included essential oil or hydrophobic compound is useful for treating. Such diseases or disorders include dermatological diseases including wounds, microbial infections, eczema, and skin cancer. The nanoemulstions are also useful in various cosmetic, medical, and food applications.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. tamanu oil) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4 or more times weekly.

As demonstrated in the Example, a nanoemulsion as described herein allows for a lower dosage of essential oil, e.g. tamanu oil, to be administered for treatment of bacterial infections as compared to the use of pure oil. For example, the amount of essential oil required may be only about 0.008-0.025% w/v, e.g. 0.017-0.021% w/v, e.g. about 0.019%.

Whilst the beneficial effects of the disclosure are particularly apparent in transdermal delivery, the utility of the disclosure is not limited and compositions according to the invention may also used for oral, intranasal, buccal, rectal, vaginal, ocular, intraperitoneal, and parenteral drug delivery.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Natural compounds, particularly essential oils (EOs), possess many advantages in cosmetics, agriculture, herbal and modern medicine. However, EOs positive effects are hindered by many drawbacks including hydrophobicity, instability and high degradation rate, volatility, and light sensitivity. Oil-in-water nanoemulsions (O/W NEs) are promising nanocarriers having high loading capacities of hydrophobic compounds. This work aimed to develop a stable NE loaded with tamanu essential oil (TMO), that has antimicrobial, wound healing, and UV protective properties, as a topical drug delivery system for the management and treatment of skin abnormalities.

O/W TMO-NE was prepared by dispersing the oil core, 10% TMO, using ultrasonic emulsification in the presence of surfactants; 3% Tween 80®, 4% Imwitor 375, and 2% Imwitor 988 as a skin penetration enhancer. The physicochemical properties of the developed NE were determined using dynamic and electrophoretic light scattering. The effect of different environmental and biological conditions (temperature, skin pH, salt, and serum proteins) on O/W TMO-NE stability were tested. Cytotoxicity of TMO-NE against human neonatal skin fibroblasts (HNDFs) was evaluated using WST-1 assay. The antimicrobial activity of TMO-NE was tested on the leading causative microorganism of dermal infection, $S.$ $aureus$, a gram-positive bacteria.

Light, green O/W TMO-NE was successfully developed using ultrasonication-based emulsification method. The formulated TMO-NE, of 101.43±1.35 nm droplet size and 0.16±0.00 PDI value, comprises 10% of TMO, 3% TWEEN 80®, 4% Imwitor 375, and 2% Imwitor 988. TMO-NE has highly negative surface charge with a value of −60.9±1.15 mV, contributing to electrostatic repulsive stability. TMO-NE demonstrated physical stability in high salt solution, PBS. TMO-NE shows over a week stability in serum-enriched cell culture media. TMO-NE also showed remarkable stability at skin pH for a month. TMO-NE shows over a week of stability in high ionic strength solution, that have divalent cations, $CaCl_2$. The fabricated TMO-NE enhanced the proliferation of the human neonatal dermal fibroblasts (HNDFs), and demonstrated minimal or no cytotoxicity at low TMO concentrations. TMO-NE has demonstrated a potent antimicrobial activity on one of the most common causative agents of skin infections, $S.$ $aureus$.

Materials and Methods

Materials

TMO (Calophyllum inophyllum L. oil) was obtained from NOW, U.S.A., Glyceryl Citrate/Lactate/Linoleate/Oleate (Imwitor 375®), and glycerol monocaprylate, type I (Imwitor 988®), were obtained from IOI Oleochemicals, Germany. Polysorbate 80 (Tween 80®), calcium chloride ($CaCl_2$), sodium hydroxide (NaOH), and hydrogen chloride (HCl) were bought from Sigma-Aldrich, US. Roswell Park Memorial Institute (RPMI-1640) media, fetal bovine serum (FBS), penicillin and non-essential amino acid (NEAA) were purchased from Gibco-Biocult Ltd., UK.

Preparation of Nanoemulsions (NE)

The formulation of O/W TMO-NE composition is composed of dispersed (hydrophobic) and continuous (hydrophilic) phases. The dispersed phase (hydrophobic core) comprised 10% TMO, 4% Imwitor 375® and 2% Imwitor 988® of the final formulation. The continuous phase included 3% Tween 80® and distilled water. The dispersed was added to the continuous phase and exposed to six bursts, each at 72 W for 45 s using the high-energy ultrasonic method (Fisherbrand™ Model 120 Sonic, Pittsburgh, US) with cooling in ice for 1 minute between each burst. A ⅛-inch sonicator probe was used to promote ultrasonic waves implementing cavitation energy that breaks down the hydrophobic core, TMO, into nano-sized oil droplets during emulsification.

Characterization of TMO-NE Droplet Size, Dispersity and ζ-Potentials

Particle size distribution and PDI of the formulated TMO-NE were measured at 25° C. using a DLS-based instrument, Malvern Zetasizer Nano ZS, UK after diluting TMO-NE at a 1:100 ratio with deionised water. The Zetasizer Nano ZS device uses a laser beam that produces light at a specific wavelength, 632 nm, and a detector for the scattered intensity at a particular angle, 173 degrees. Measurements of the scattered light were translated to numbers reflecting TMO-droplets sizes on the Zetasizer software. ζ-potentials (ZP) of TMO-NEs samples were diluted at a 1:100 ratio and measured using electrophoretic light scattering on Malvern Zetasizer Nano ZS. TMO-NE average droplet size also investigated in PBS at a 1:100 ratio using DLS.

Effect of Storage Temperature, Salt, and pH Conditions on TMO-NE

The stability of the prepared TMO-NE formulation was investigated in different conditions, including heat, pH, and salts. The physical stability of prepared samples was tested against several temperatures, including 4, 24, and 37° C. overnight for a month. The effect of pH on the prepared emulsions was determined by incubating TMO-NEs in different media having pH values of 4, 5, and 7. TMO-NE samples were also incubated in 100 mM $CaCl_2$) and 1× (phosphate buffer saline) PBS to assess the effect of salt on TMO-NEs stability.

Cell Preparation for In Vitro Assessments

Human neonatal dermal fibroblasts (HNDFs) were grown and maintained in Dulbecco's modified Eagle's medium and high glucose supplemented with 10% foetal bovine serum, 1% MEM non-essential amino acid, 100 U/mL penicillin, and 100 mg/mL streptomycin. HNDFs with 80% confluency were detached from the culture dish using 0.25% trypsin-EDTA solution, collected in a 15 ml falcon tube and centrifuged at 1500 rpm for 5 minutes. Then, the cell pellet was passaged into a new culture dish (split ratio 1:2) containing fresh media. All the media used in cell culture were supplied by (Thermo Fisher Scientific, USA). For cytotoxicity assay, cells were seeded on a 96-well culture dish (100,000 cells/well with 98% cell viability) containing fresh media.

Cell Viability and Cytotoxicity Assay of TMO-NE

WST-1 assay kit (Abcam, ab155902) was used according to manufacturer's protocol to measure cell proliferation, viability, and cytotoxicity of HNDFs cultured with different concentrations of nano-emulsion. The absorbance was measured at 440 nm in a plate reader (Multiskan SkyHigh Microplate Spectrophotometer, ThermoFisher Scientific, US). Each sample was run in triplicate and the average absorbance value was calculated. The background value was corrected against a blank control and the effect of TMO-NE was compared to cell controls at zero and 24 hours of cell culture.

Antibacterial Activity of TMO-Loaded NEs:

Minimum Inhibitory Concentration (MIC) and Minimum Bactericidal Concentration (MBC) Test MIC of the TMO-loaded NE was investigated using broth microdilution method in compliance with the Clinical and Laboratory Standards Institute (CLSI) guidelines; Performance Standards for Antimicrobial Susceptibility Testing (M100, 2020) and Methods for Dilution Antimicrobial Susceptibility Tests for Bacteria That Grow Aerobically (M07, 2018). Two-fold serial dilutions of TMO-loaded NE were prepared in a 96-well plate, starting from 0.156% till 0.0097% of TMO concentration. $S.$ $aureus$ suspension at $5\times10^5$ colony forming unit (CFU) $mL^{-1}$ were prepared in Muller Hinton agar (MHB) then added to each well. 0.005% of TTC was applied on each test dilution to find out the MIC. The prepared microdilution test samples were incubated for 18 hours incubation at 37° C., the MICs were determined quantitively based on the measured absorbance readings at 485 nm using Multiskan SkyHigh Microplate Spectrophotometer (ThermoFisher Scientific, US) To conduct MBC test, 10 μl of each test well having no bacterial growth, based on the MIC results, were sub-cultured on MHA plate. Following overnight incubation of the sub-cultured plates at 37° C., MBC was determined at the highest dilution of TMO-NEs showing no growth of S. aureus. We have compared the antimicrobial activity of the Tamanu oil aqueous solution to tamanu oil loaded nanoemulsion, and we found that the antimicrobial activity of the tamanu oil loaded nanoemulsion is 16 folds more potent than the tamanu oil aqueous solution. We have also tested the functional stability of the tamanu oil loaded nanoemulsion after a week of storage at 4° C. on S. aureus, and the results show that the developed nanoemulsion retained their antimicrobial activity for at least a week (bactericidal effect at 0.019% of loaded TMO).

Statistical Analysis

Statistical data were expressed as mean±standard deviation (SD).

Results and Discussion

Characterization of TMO-NE

The physio-chemical properties of TMO-NE including average droplet size (Z-average) and PDI and ζ-potential were investigated using dynamic and electrophoretic light scattering respectively. The prepared TMO-NE has a hydrodynamic size of 98.2±2.22 with a PDI of 0.15±0.00 indicating that TMO-NE has monodispersed oil droplets (FIG. 1). This implies that TMO-NE is less prone to be affected by the destabilization mechanisms. The surface charge or ζ-potential of TMO-NE was highly negative with a value of −60.9±1.15, therefore demonstrating strong electrostatic repulsion forces between the dispersed oil droplets, that contribute to long-term colloidal stability (FIG. 1). It is well known that ζ-potential values of −/+30 mV and above contributes to additional physical stability to NE formulations. These results, size, PDI, and ζ-potential measurement, indicate that TMO-NE droplets have desirable physical stability for medical and cosmetic applications.

Figure 2:
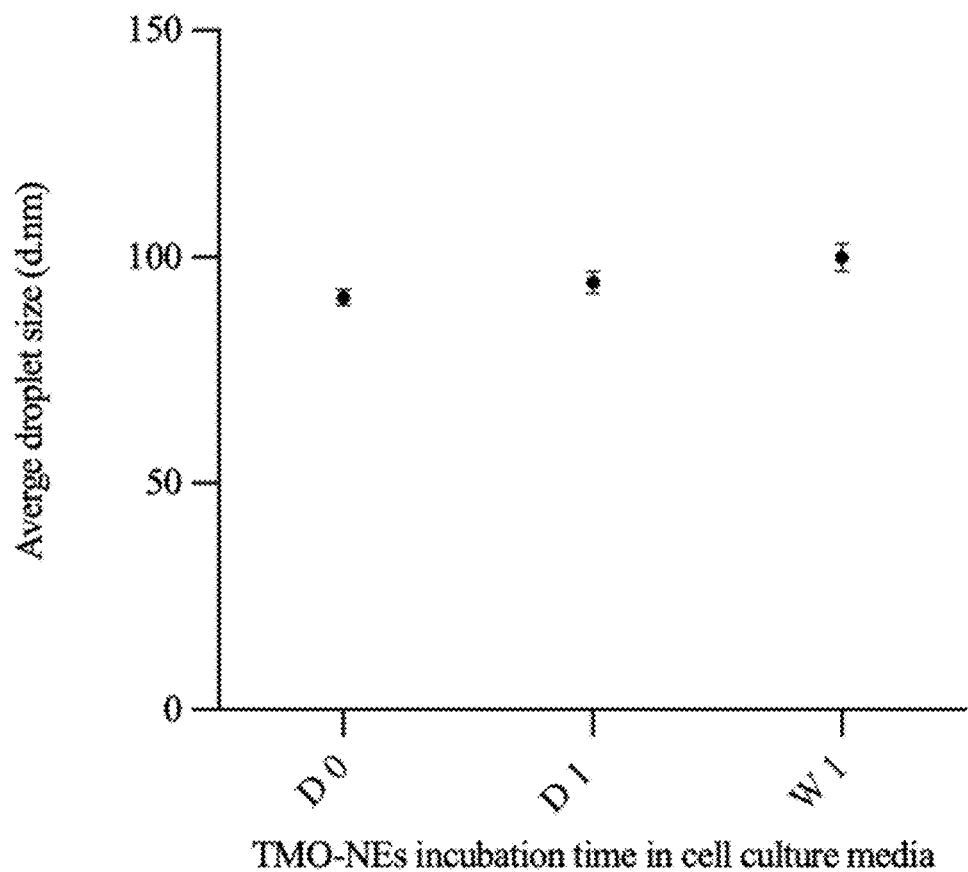
FIG. 2. Stability of TMO-NE in cell culture media.
Figure 3:
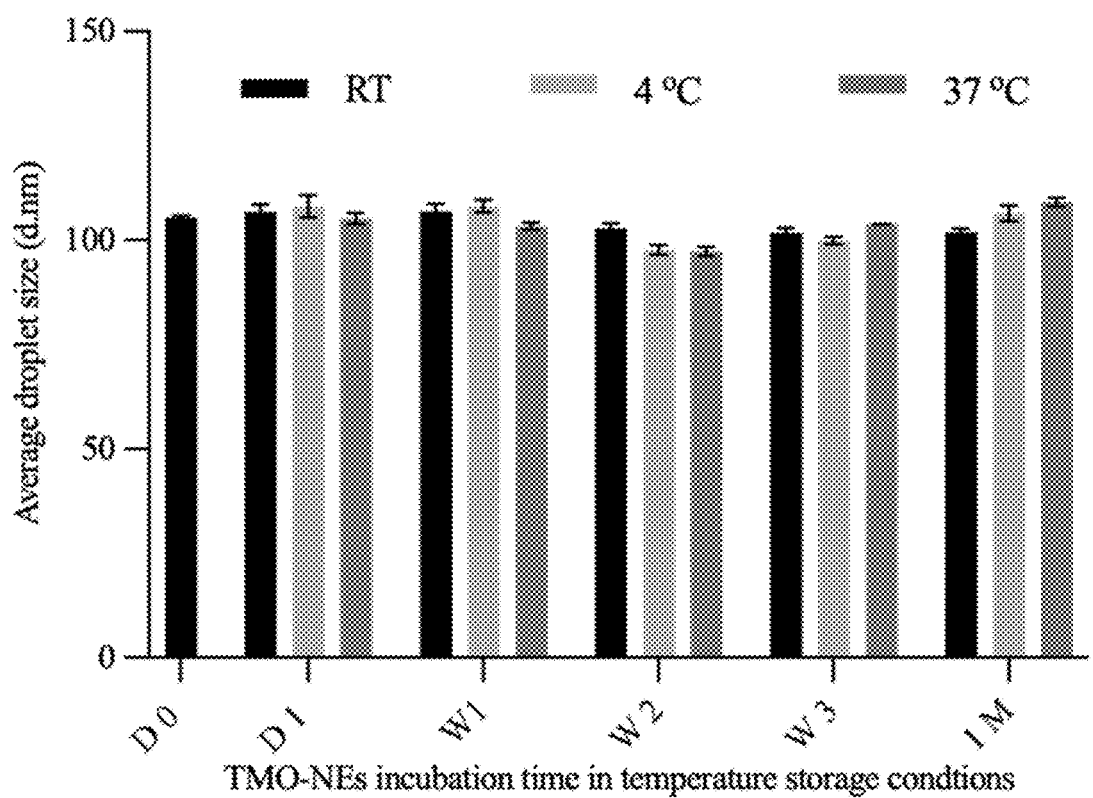
FIG. 3. Stability of the TMO-NE in different temperature storage conditions.
Figure 4:
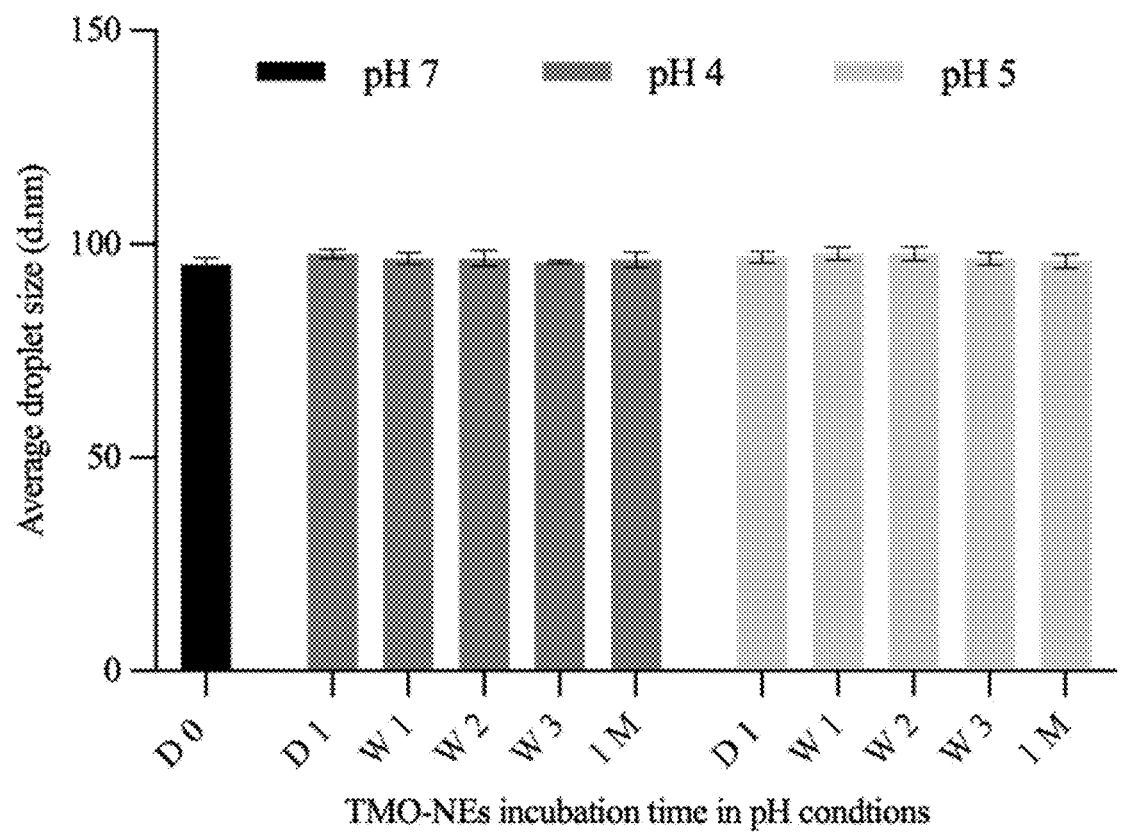
FIG. 4. Stability of TMO-NE under varying pH conditions.
Figure 5:
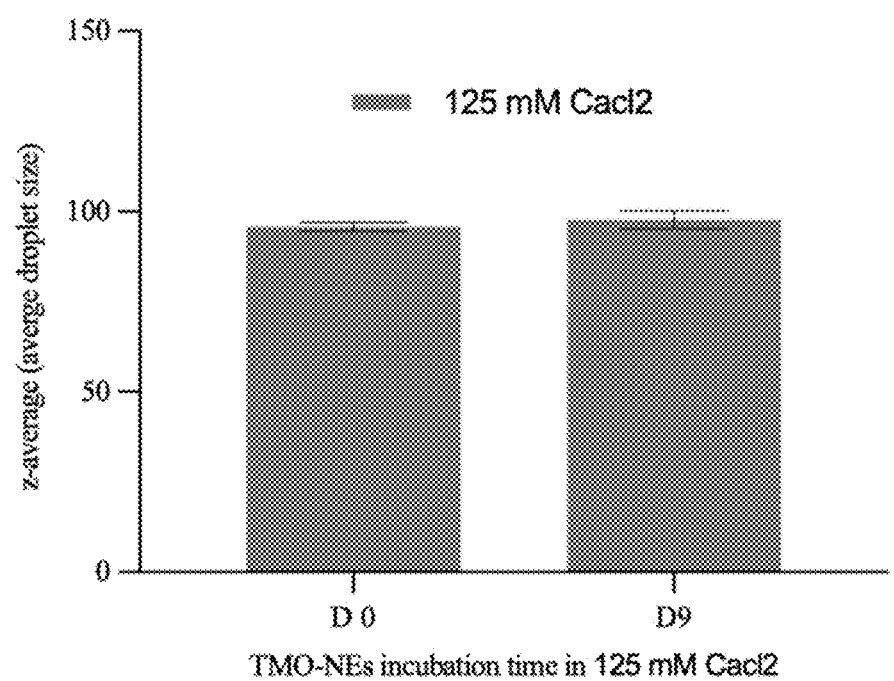
FIG. 5. Stability of TMO-NE in salt and metal ions.

Stability against physical and chemical factors, such as salt and pH, involved in biological applications is an important aspect for NEs pharmaceutical performance, and thus therapeutic outcomes. PBS, which is the most common isotonic solution used in cell cultures and in vitro assay, composition has high salt concentration that can affect the functionality of stabilizers or surfactants resulting in desorption and phase separation. Therefore, the stability of TMO-NE in PBS was tested and showed negligible change in both Z-average and PDI, 94.16±1.11, PDI 0.15±0.01 respectively. The incubation of nanomaterials in serum proteins, minerals, and salts, like cell culture media during in vitro or in vivo applications can cause instant or over time physical instability. TMO-NE was evaluated in RPMI media comprising 10% serum proteins and maintained its physical stability for a week with slight increase in droplet size at day 7 by 8.7±1.26 with no creaming or sedimentation observed (FIG. 2). Another import aspect for pharmaceutical application is that the developed drug delivery system remains stable in different storage conditions and during in vitro assays, that are conducted at human body temperature, 37° C. We found that storing TMO-NE at 4° C. and room temperature conditions show negligible change in droplet size. TMO-NE was also investigated in 37° C. condition, showing size increase by only 3.9±0.87 nm after one month of incubation (FIG. 3). It is worth mentioning that the PDI of TMO-NE remained below 0.2, indicating monodispersity of the TMO droplets. pH levels can also affect the functionality of nanomaterials; therefore, we investigated the effect of skin pH, 4 and 5, on the stability of TMO-NE formulation. The results show no significant change on TMO-NE droplet size in both pH 4 and pH 5 (FIG. 4). These data suggest that the developed TMO-NE formulation can maintain stability in different storage temperatures and during in vitro assays on dermal tissues.

NEs can be formulated into different dosage forms including liquids and semi-solids such as gels and creams. One of the main methods to transform NEs into nanoemulgels is using a divalent cation such as $CaCl_2$ salts, for crosslinking naturally occurring polymers, like sodium alginate. We used this cross-linking technique and $CaCl_2$ as a proof-of-concept stability study of the developed TMO-NE formulation. TMO-NE was incubated in 125 mM $CaCl_2$ solution over a week and demonstrated good stability with a minimal increase in size by only 2 nm. This shows that TMO-NEs can be successfully encapsulated into alginate-based nanoemulgels crosslinked by high concentration of $CaCl_2$, up to 125 mM, up to 9 days of incubation at room temperature.

Figure 6:
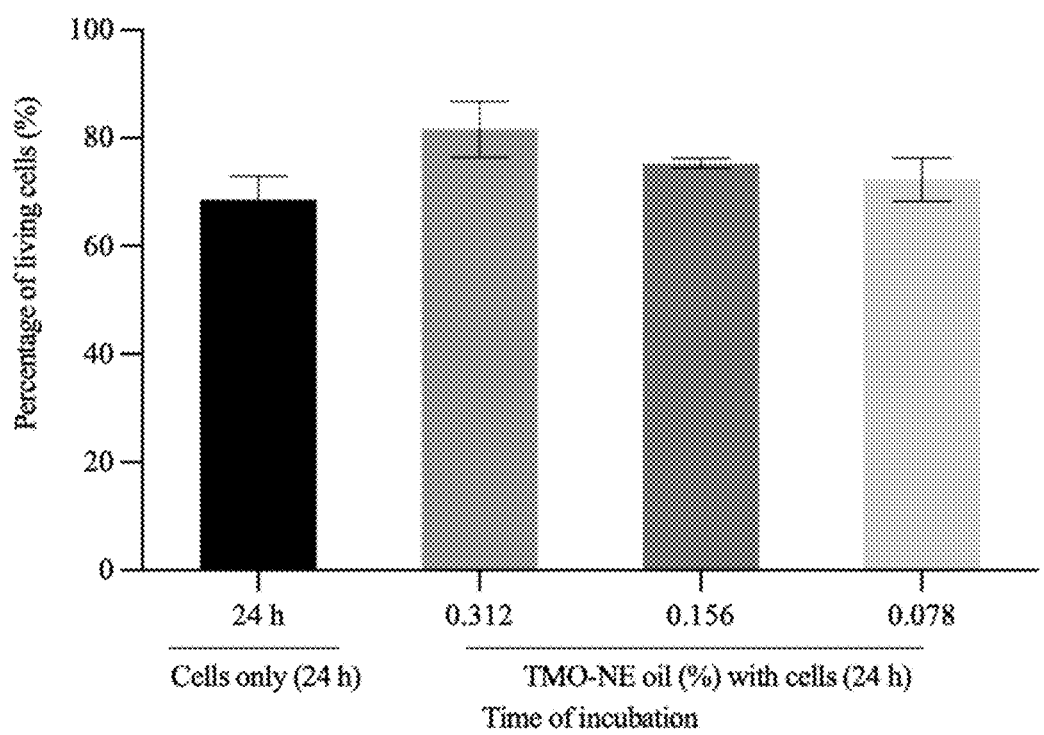
FIG. 6. Cytotoxicity of the TMO-NE on fibroblast skin cells.
Figure 7A:
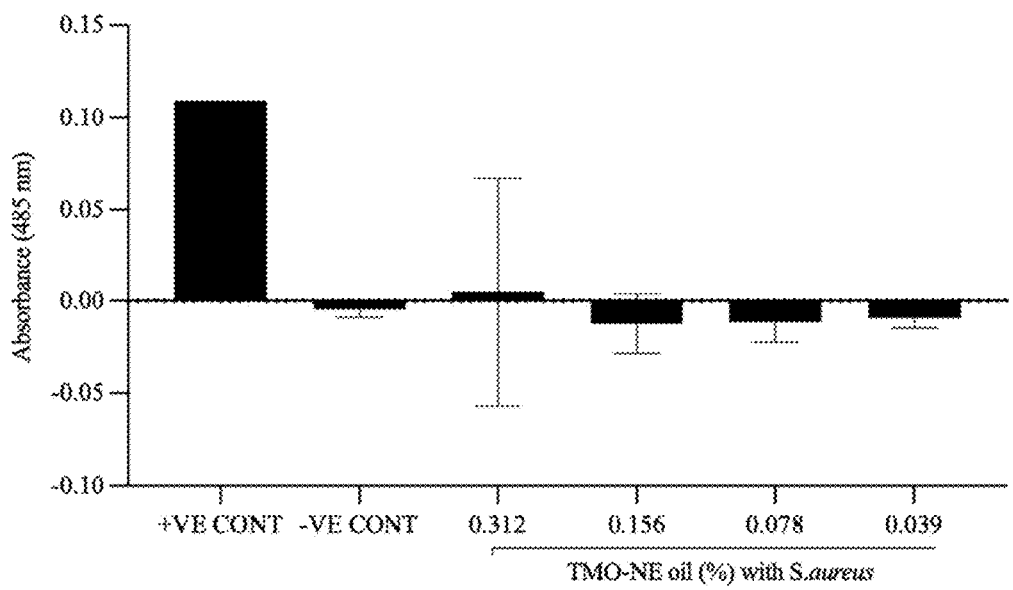
FIGS. 7A-B. Antimicrobial activity of TMO-NE. (A) represents the absorbance readings (485 nm) of the +VE (*S. aureus* suspension) control and negative −VE control (Muller Hinton) and different concentrations of TMO loaded NEs represented as TMO concentration (0.312, 0.156, 0.078, 0.039, 0.019, and 0.009). (B) represents the minimum inhibitory test based on the microdilution test in (A). The microdilution test samples (+VE and −VE controls, TMO-NE concentrations) were sub-cultured on Muller Hinton agar.
Figure 7B:
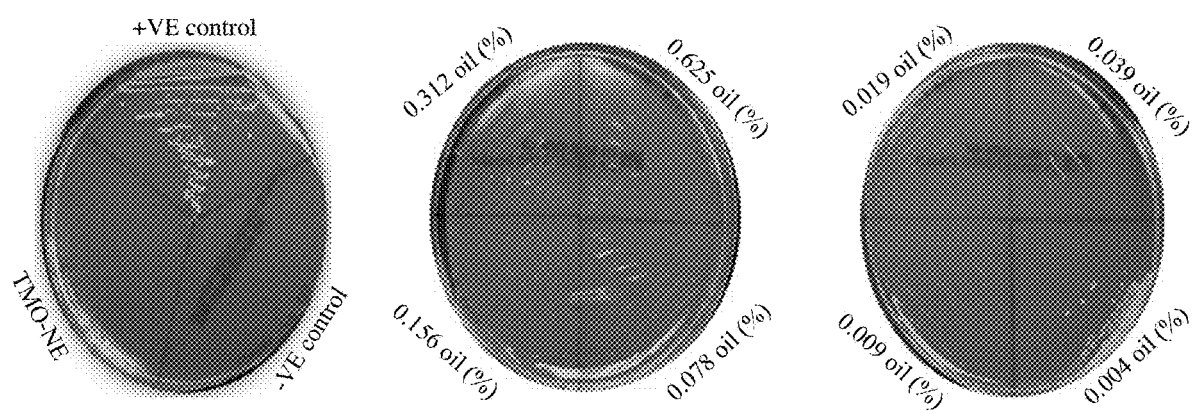

To examine the effect of TMO-NE on dermal cells, viability of HNDFs was evaluated through measuring the percentage of living cells after 24 hours of incubation within different concentrations of TMO-NE (FIG. 6). Our data indicated that high concentrations of TMO-NE (0.312 & 0.156 oil %) promoted cell proliferation and viability compared to cell control after 24 hours of incubation, while lower concentrations of TMO-NE (0.078 oil %) had no effect on the cells. To the best of our knowledge, TMO-NE has not been previously discovered as a cell proliferation promoter of HNDFs. Thus, our findings have indicated that TMO-NE can promote human dermal fibroblasts proliferation and thus would be useful in wound healing.

To investigate the antimicrobial activity of TMO-NE, S. aureus, a leading causative agent of skin infections, was used as a model. TMO-NE showed strong antimicrobial activity starting from the lowest dilution (1.25 oil %) to the highest dilution (0.009 oil %). The MBC value of TMO-NE on S. aureus was at 0.019 oil %, showing remarkable bactericidal effect. This study suggests that TMO-NE can be used as an additive or medication against bacterial infection in the field of medicine and cosmeceuticals.

CONCLUSION

TMO-NE was successfully prepared using ultrasonication with a droplet size of 98.2±2.22 and PDI of 0.15±0.00. The dispersed TMO nanodroplets were stabilized using Tween® 80 and PEG 400 as a surfactant and cosurfactant, respectively. The formulation of TMO-NE was also functionalized with Imwitor® 988 for enhancing penetration and delivery of the encapsulated cargos to skin tissues. The developed TMO-NE demonstrated physical stability in different salt concentrationS including PBS and $CaCl_2$). TMO-NE also retained its average droplet size in different storage temperatures. The incubation of TMO-NE has also maintained stability in in vitro cell culture conditionS, particularly RPMI media at 37° C. for a week. The effect of the acidic level of skin pH was also minimal on the TMO-NE average droplet size. These results suggest that TMO-NE is a useful formulation toward different in vitro and in vivo applications, particularly on dermal cells.

Safety and toxicity levels of nanomaterials is an important aspect in biological applications. TMO-NE cytotoxicity levels were tested on skin cells, HDNFs, and showed a proliferation-promoting effect and minimal or no toxicity at oil concentrations starting from 0.312% of encapsulated TMO. The estimated safe concentrations of TMO-NE demonstrated potent antimicrobial activity *S. aureus*. These results suggest that TMO-NE can be applied safely for the protection of skin against environmental effects such as UV light exposure and oxidation. TMO-NE can also be used as a pharmaceutical formulation for the management of dermatological diseases including infected wounds, microbial infections, eczema, and cancer.

ACKNOWLEDGEMENT

The authors extend their appreciation to the Deputyship for Research & Innovation, Ministry of Education in Saudi Arabia for funding this research work through the project number IFPRC-121-142-2020 and King Abdulaziz University, DSR, Jeddah, Saudi Arabia.

REFERENCES

[1] Nastiti C M R R, Ponto T, Abd E, Grice J E, Benson H A E, Roberts M S. Topical Nano and Microemulsions for Skin Delivery. Pharmaceutics. 2017; 9:37.
[2] Tayeb H H, Sainsbury F. Nanoemulsions in drug delivery: formulation to medical application. Nanomedicine. 2018; 13:2507-25.
[3] Salim N, Ahmad N, Musa S H, Hashim R, Tadros T F, Basri M. Nanoemulsion as a topical delivery system of antipsoriatic drugs. RSC Advances. 2016; 6:6234-50.
[4] Ramsey J T, Shropshire B C, Nagy T R, Chambers K D, Li Y, Korach K S. Essential Oils and Health. The Yale journal of biology and medicine. 2020; 93:291-305.
[5] Ali H, Al-Khalifa A R, Aouf A, Boukhebti H, Farouk A. Effect of nanoencapsulation on volatile constituents, and antioxidant and anticancer activities of Algerian *Origanum glandulosum* Desf. essential oil. Scientific Reports. 2020; 10:2812.
[6] Ginigini J, Lecellier G J, Nicolas M, Nour M, Hnawia E, Lebouvier N, et al. Chemodiversity of Calophyllum inophyllum L. oil bioactive components related to their specific geographical distribution in the South Pacific region. PeerJ. 2019; 7:e6896-e.
[7] Raharivelomanana P, Ansel J-L, Lupo E, Mijouin L, Guillot S, Butaud J-F, et al. Tamanu oil and skin active properties: from traditional to modern cosmetic uses. OCL. 2018; 25:D504.
[8] Léguillier T, Lecsö-Bornet M, Lémus C, Rousseau-Ralliard D, Lebouvier N, Hnawia E, et al. The Wound Healing and Antibacterial Activity of Five Ethnomedical Calophyllum inophyllum Oils: An Alternative Therapeutic Strategy to Treat Infected Wounds. PLoS One. 2015; 10:e0138602.
[9] Said T, Dutot M, Martin C, Beaudeux J L, Boucher C, Enee E, et al. Cytoprotective effect against U V-induced DNA damage and oxidative stress: role of new biological U V filter. European journal of pharmaceutical sciences: official journal of the European Federation for Pharmaceutical Sciences. 2007; 30:203-10.
[10] Yimdjo M C, Azebaze A G, Nkengfack A E, Meyer A M, Bodo B, Fomum Z T. Antimicrobial and cytotoxic agents from Calophyllum inophyllum. Phytochemistry. 2004; 65:2789-95.
[11] Nguyen V L, Truong C T, Nguyen B C Q, Vo T V, Dao T T, Nguyen V D, et al. Anti-inflammatory and wound healing activities of calophyllolide isolated from Calophyllum inophyllum Linn. PLoS One. 2017; 12:e0185674.
[12] Urbánková L, Kagparkova V, Egner P, Rudolf O, Korábková E. Caseinate-Stabilized Emulsions of Black Cumin and Tamanu Oils: Preparation, Characterization and Antibacterial Activity. Polymers (Basel). 2019; 11:1951.
[13] Pham D H, Nguyen T T. Preparation of Tamanu Oil Nanoemulsions by Phase Inversion Temperature. IOP Conference Series: Materials Science and Engineering. 2020; 991:012116.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. An oil-in-water nanoemulsion, consisting of
8-12% w/v essential oil;
1-5% w/v polysorbate 80 surfactant;
2-6% w/v glyceryl citrate/lactate/linoleate/oleate co-surfactant; and
1-5% w/v glycerol monocaprylate, type I.
2. An oil-in-water nanoemulsion, consisting of
10% w/v essential oil;
3% w/v polysorbate 80 surfactant;
4% w/v glyceryl citrate/lactate/linoleate/oleate co-surfactant; and
2% w/v glycerol monocaprylate, type I.

* * * * *